United States Patent [19]

Pissiotas

[11] 3,935,250

[45] Jan. 27, 1976

[54] N-LOWER ALKYL, N-LOWER ALKYLIMINOMETHYL CARBAMIC ACID ESTERS OF αNAPHTHOL AND SUBSTITUTED PHENOLS

[75] Inventor: Georg Pissiotas, Lorrach, Germany

[73] Assignee: Ciba-Geigy Corporation, Ardsley, N.Y.

[22] Filed: Oct. 1, 1973

[21] Appl. No.: 402,648

[30] Foreign Application Priority Data
Oct. 12, 1972  Switzerland.................... 14963/72
July 30, 1973  Switzerland.................... 10999/73

[52] U.S. Cl...260/346.2 R; 260/240 G; 260/327 M; 260/330.5; 260/340.9; 260/468 E; 260/471 C; 260/479 C; 424/275; 424/278; 424/285; 424/300
[51] Int. Cl.$^2$..................................... C07D 307/79
[58] Field of Search ..... 260/346.2 R, 479 C, 471 C, 260/468 E, 340.9, 330.5, 327 M, 240 G

[56] References Cited
UNITED STATES PATENTS
3,564,041  2/1971  Farrissey et al..................... 260/479

FOREIGN PATENTS OR APPLICATIONS
2,259,218  6/1973  Germany

*Primary Examiner*—John M. Ford
*Assistant Examiner*—Bernard I. Dentz
*Attorney, Agent, or Firm*—Harry Falber; Frederick H. Rabin

[57] ABSTRACT

Formamidines of the formula

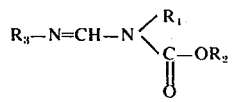

wherein $R_1$ represents hydrogen, alkyl, alkenyl or alkinyl, $R_2$ represents α-naphthyl or substituted phenyl, and $R_3$ represents alkyl, alkenyl, alkinyl, aralkyl or cycloalkyl, a process for their manufacture, and their use in pest control.

6 Claims, No Drawings

N-LOWER ALKYL, N-LOWER ALKYLIMINOMETHYL CARBAMIC ACID ESTERS OF < NAPHTHOL AND SUBSTITUTED PHENOLS

The present invention relates to formamidines or salts thereof, process for their manufacture, and to their use in pest control.

The formamidines have the formula

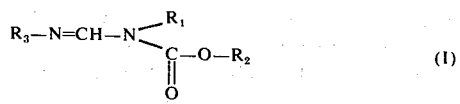

wherein $R_1$ represents hydrogen, alkyl, alkenyl or alkinyl, $R_2$ represents α-naphthyl or substituted phenyl, and $R_3$ represents alkyl, alkenyl, alkinyl, aralkyl or cycloalkyl.

Possible salts of compounds of the formula I are those of organic or inorganic acids.

The alkyl, alkenyl or alkinyl groups represented by $R_1$ and $R_3$ have one to 18 carbon atoms in the chain, the alkenyl and alkinyl chains containing from three to 18 carbon atoms, but preferably one to four and three to five carbon atoms respectively, in the chain. These groups can be straight-chain or branched, substituted or unsubstituted. Suitable substituents are preferably halogen atoms. By halogen is meant fluorine, chlorine, bromine and/or iodine. Examples of such groups include: methyl, ethyl, trifluoromethyl, chloroethyl, propyl, ispropyl, n-, i-, sec.- and tert. butyl, allyl, metallyl, propargyl, n-butinyl, isobutinyl.

Possible substituents at the phenyl group represented $R_2$ are chiefly one or more similar or different halogen atoms, such as fluorine, chlorine, bromine and/or iodine and/or alkyl with one to five carbon atoms, haloalkyl with one to four carbon atoms, alkoxy with one to four carbon atoms, alkoxyalkyl with one to four carbon atoms in each of the moities, alkylthio with one to four carbon atoms, alkinyloxy with three to four carbon atoms, dialkylamino with one to four carbon atoms, dialkenylamino, dialkinylamino, hydroxy, cyano and/or nitro group, also cyclopentyl, monoalkylaminomethyleneamino, dialkylaminomethyleneimino,

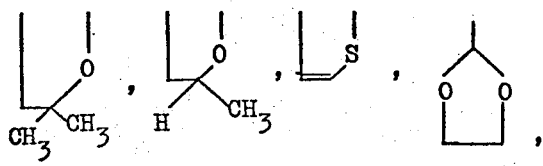

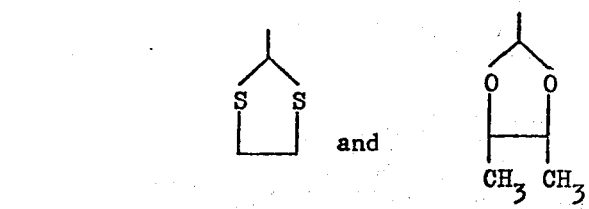

groups.

Aralkyl is to be understood as meaning in particular the benzyl or phenethyl groups which are unsubstituted or substituted by halogen, in particular chlorine, alkyl with one to four carbon atoms and/or alkoxy with one to four carbon atoms.

Preferred compounds on account of their action are those of formula I, wherein $R_1$ represents methyl, $R_2$ represents α-naphthyl, 2-methylphenyl, 3-methylphenyl, 2-chlorophenyl, 2-isopropylphenyl, 3-isopropylphenyl, 3-methyl-5-isopropylphenyl, 2-chloro-5-tert.butylphenyl, 3,4-dimethylphenyl, 3,4,5-trimethylphenyl, 3,5-dimethyl-4-methylthiophenyl, 3,5-di-tert.butylphenyl, 2-isopropoxyphenyl, 2-allyloxyphenyl, 3-methyl-4-dimethyl-aminophenyl, 3,5-dimethyl-4-dimethylaminophenyl, 3,5-dimethyl-4-diallylaminophenyl, 1,3-dioxolan-2-yl-phenyl, 1,3-diothiolan-2-yl-phenyl, (4,5-dimethyl-1,3-dioxolan-2-yl)-phenyl, 3-(1-methylbutyl)-phenyl, 2-sec.butylphenyl, 3-(1-ethylpropyl)-phenyl, 2,3-xylyl, 3-tert.butylphenyl, 3-sec.butylphenyl, 3,5-diisopropylphenyl, 2-chloro-5-isopropylphenyl, 3,5-dimethyl-4-methoxyphenyl, 3-allyloxyphenyl, 2-propargyloxymethoxyphenyl, 2-γ-methylthiopropylphenyl, 3-(α-methoxymethyl)-2-propenylphenyl, 4-(methyl-propargylamino)-3,5-xylyl, 4-(methyl-γ-chloroallylamino)-3,5-xylyl, 2-(ethylpropargylamino)-phenyl, 2-chloro-4,5-dimethylphenyl, 2-(2-propinyloxy)-phenyl, 3-(2-propinyloxy)-phenyl, 2-dimethylaminophenyl, 2-diallylaminophenyl, 3-methyl-4-dimethylaminomethyleneiminophenyl, 3-dimethylaminomethyleneiminophenyl, 3-isopropyl-4-methylthiophenyl, 5,6,7,8-tetrahydronaphthyl, 2-(methyl-propargylamino)-3-tolyl, 4-(dipropargylamino)-3,5-xylyl, 2-(allyl-isopropylamino)-phenyl, 3-(allyl-isopropylamino)-phenyl, 3-methoxymethoxyphenyl, 2-cyclopentylphenyl, 2-(1-butin-3-yl-oxy)-phenyl or 2-(1-methoxy-2-propoxy)-phenyl,

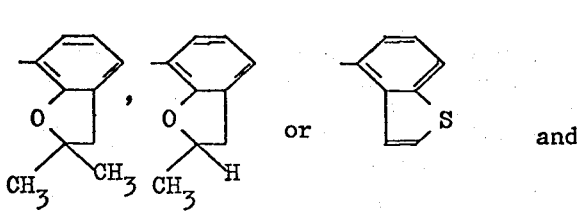

$R_3$ represents alkyl with one to 12 carbon atoms, alkenyl with three to four carbon atoms, alkinyl with three to five carbon atoms, benzyl or phenethyl which is unsubstituted or substituted by one or more chlorine atoms and/or methyl, cyclopentyl, or cyclohexyl.

The compounds of the formula I can be manufactured by methods which are known per se, e.g. by reacting formamidines of the formula

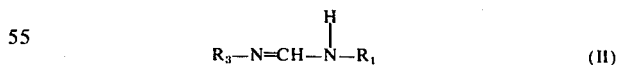

with an ester of chloroformic acid of the formula

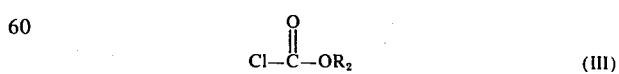

in the presence of an acid acceptor. In the formulae II and III, $R_1$ to $R_3$ have the same meanings as given for the formula I.

Examples of suitable acid acceptors are: formamidines of the formula II; tertiary amines, such as triethylamine, dimethylaniline, pyridine, inorganic bases, such as hydroxides and carbonates of alkali and alkaline earth metals, preferably sodium and potassium carbonate.

The reaction is carried out preferably in solvents or diluents which are inert towards the reactants. Examples of suitable solvents or diluents are: aromatic hydrocarbons, such as benzene, toluene, benzenes, halogenated hydrocarbons, chlorobenzene, polychlorobenzene, bromobenzene, chlorinated alkanes with one to three carbon atoms; ethers, such as dioxan, tetrahydrofuran; esters, such as ethyl acetate; ketones, such as methyl ethyl ketone, diethyl ketone, nitriles etc.

Some of the starting materials of the formula II and III are known compounds which can be manufactured by methods which are known per se.

The compounds of the formula I display a broad biocidal activity and can be used for combating diverse plant and animal pests and as plant regulators and abscission agents.

In particular, however, they possess insecticidal and acaricidal properties and may be used against all development stages, e.g. eggs, larvae, pupae, nymphs and adults, of insects and representatives of the order Acarina, for example against insects of the families: Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culicidae, Tripulidae, Stomoxydae, Muscidae, Calliphoridae, Trypetidae, Pulicidae, as well as Acaridae of the families: Ixodidae, Argasidae, Tetranychidae, Dermanyssidae.

The insecticidal or acaricidal action can be substantially broadened and adapted to given circumstances by the addition of other insecticides and/or acaricides. Examples of suitable additives are: organic phosphorus compounds, derivatives of nitrophenols, formamidines, ureas, carbamates, and/or chlorinated hydrocarbons.

The active substances of the formula I are also suitable for combating representatives of the division Thallophyta, e.g. viruses, bacteria and fungi. They thus possess fungicidal properties against phytopathogenic fungi on various cultivated plants, such as cereals, maize, rice, vegetables, ornamental plants, fruit trees, vines, farm products, etc.

With the new active substances it is possible to control or destroy fungi occurring on fruit, blossom, leaves, stems, tubers and roots, and from which parts of plants which grow later then also remain free. The active substances of the formula I are active in particular against phytopathogenic fungi belonging to the following classes: Oomycetes, Zygomycetes, Ascomycetes, Basidiomycetes, Denteromycetes.

In addition, the new active substances can also be used for treating seeds, fruit, tubers etc., and protecting them from fungus infections, for example from smut fungi of all kinds, such as Ustilaginales, and for combating phytopathogenic nematodes.

The compounds of the formula I may be used as pure active substance or together with suitable carriers and/or additives. Suitable carriers and additives can be solid or liquid and correspond to the substances conventionally used in formulation technique, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:
Solid forms:
 Dusts, Tracking agents, granules, coated granules, impregnated granules and homogeneous granules.
Liquid forms:
 a. active substances which are dispersible in water: wettable powders, pastes, emulsions;
 b. solutions.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:
Dusts The following substances are used to manufacture (a) a 5% and (b) a 2% dust:

| a. | 5 parts of active substance |
| | 95 parts of talcum |
| b. | 2 parts of active substance |
| | 1 part of highly disperse silicic acid |

97 parts of talcum.

The active substances are mixed with the carriers and ground.
Granules

The following substances are used to produce 5% granules:

| 5 | parts of active substance, |
| 0.25 | parts of epichlorohydrin, |
| 0.25 | parts of cetyl polyglycol ether, |
| 3.50 | parts of polyethylene glycol, |
| 91 | parts of kaolin (particle size 0.3 - 0.8 mm). |

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.
Wettable powder:

The following constituents are used for the preparation of (a) a 40%, (b) and (c) a 25%, and (d) a 10% wettable powder:

| a. | 40 | parts of active substance, |
| | 5 | parts of sodium lignin sulphonate, |
| | 1 | part of sodium dibutyl-naphthalene sulphonate, |
| | 54 | parts of silicic acid. |
| b. | 25 | parts of aactive substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silicic acid, |
| | 19.5 | parts of Champagne chalk, |

```
 28.1    parts of kaolin
c. 25    parts of active substance,
   2.5   parts of isooctylphenoxy-polyoxyethylene-ethanol,
   1.7   parts of Champagne chalk/hydroxyethyl celulose
         mixture (1:1),
   8.3   parts of sodium aluminium silicate,
  16.5   parts of kieselguhr,
  46     parts of kaolin.
d. 10    parts of active substance,
   3     parts of a mixture of the sodium salts of
         saturated fatty alcohol sulphates,
   5     parts of naphthalenesulphonic acid/formaldehyde
         condensate,
  82     parts of kaolin.
```

The active substances are intimately mixed, in suitable mixers, with the additives, the mixture being then ground in the appropriate mills and rollers. Wettable powders are obtained which can be diluted with water to give suspensions of any desired concentration.
Emulsifiable concentrates:

The following substances are used to produce (a) a 10% and (b) a 25% emulsifiable concentrate:

```
a. 10    parts of active substance,
   3.4   parts of epoxidised vegetable oil,
  13.4   parts of a combination emulsifier consisting
         of fatty alcohol polyglycol ether and alkyl-
         aryl sulphonate calcium salt,
  40     parts of dimethylformamide,
  43.2   parts of xylene,
  25     parts of active substance,
   2.5   parts of epoxidised vegetable oil,
  10     parts of an alkylarylsulphonate/fatty alcohol-
         glycol ether mixture,
   5     parts of dimethylformamide,
  57.5   parts of xylene.
```

From these concentrates it is possible to produce, by dilution with water, emulsions of any desired concentration.
Spray:

The following constituents are used to prepared a 5% spray:

```
5  parts of active substance,
1  part of epichlorohydrin,
94 parts of benzene (boiling limits 160°C–190°C).
```

EXAMPLE 1

Manufacture of N-methyl-N'-methyl-N'-(2-isopropylphenyloxycarbonyl)-formamidine 30 g of chloroformic acid-O-isopropylphenyl ester are added dropwise with stirring to a solution of 22 g of N,N'-dimethyl formamidine in 250 ml of toluene (dry), the temperature being kept between 5°–10°C. After the reaction mixture has been stirred for 12 hours at room temperature, the hydrochloride salt of the formamidine simultaneously used as base in filtered off, washed with toluene, and the toluene solution evaporated in vacuo to yield the product of the formula

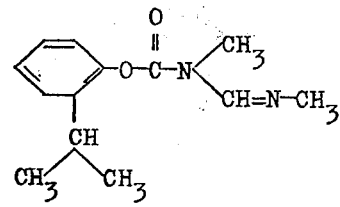

with a refractive index of $n_D^{25} = 1.5216$.

The following compounds are also manufactured in analogous manner:

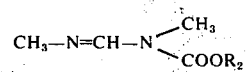

| $R_2$ | Physical Data |
|---|---|
| ![structure: 2-(isopropyl-dioxy)phenyl with O-C(CH₃)₂] | $n_D^{25°} = 1,5350$ |
| ![3,4-dichlorophenyl] | b.p.: 115°C/0,04 Torr |
| ![2-methylphenyl] | b.p.: 39°C/0,04 Torr |
| ![4-methylphenyl] | b.p.: 103°C/0,03 Torr |
| ![2,6-dimethyl-4-methylthiophenyl] | b.p.: 147°C/0,08 Torr |

| $R_2$ | Physical Data |
|---|---|
| 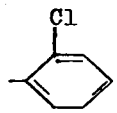 | b.p.: 58-59°C |
| 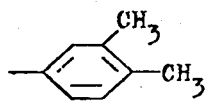 | b.p.: 39°C/0,04 Torr |
| 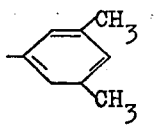 | b.p.: 39°C/0,04 Torr |
| 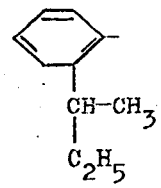 | b.p. 38°C/0,04 Torr |
| 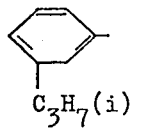 | b.p. 110°C/0,15 Torr |
| 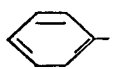 | b.p. 94°C/0,02 Torr |
| 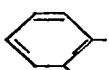 | b.p. 88-89°C/0,07 Torr |
| 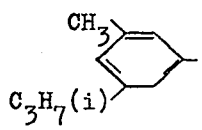 | b.p. 55°C/0,02 Torr |
| 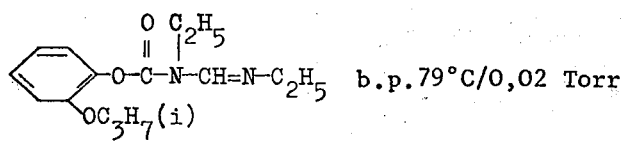 | b.p. 79°C/0,02 Torr |

-continued
| R₂ | R₂ |
|---|---|
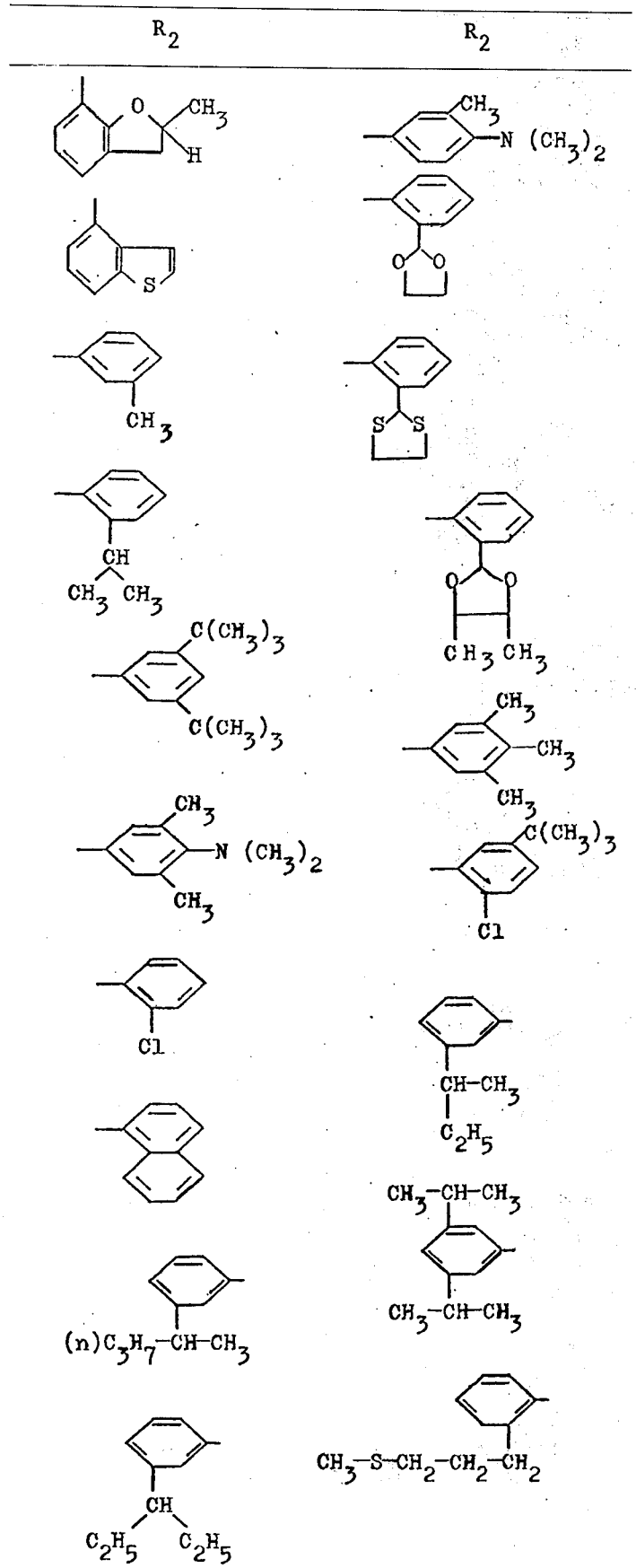

-continued
| $R_2$ | $R_2$ |
|---|---|
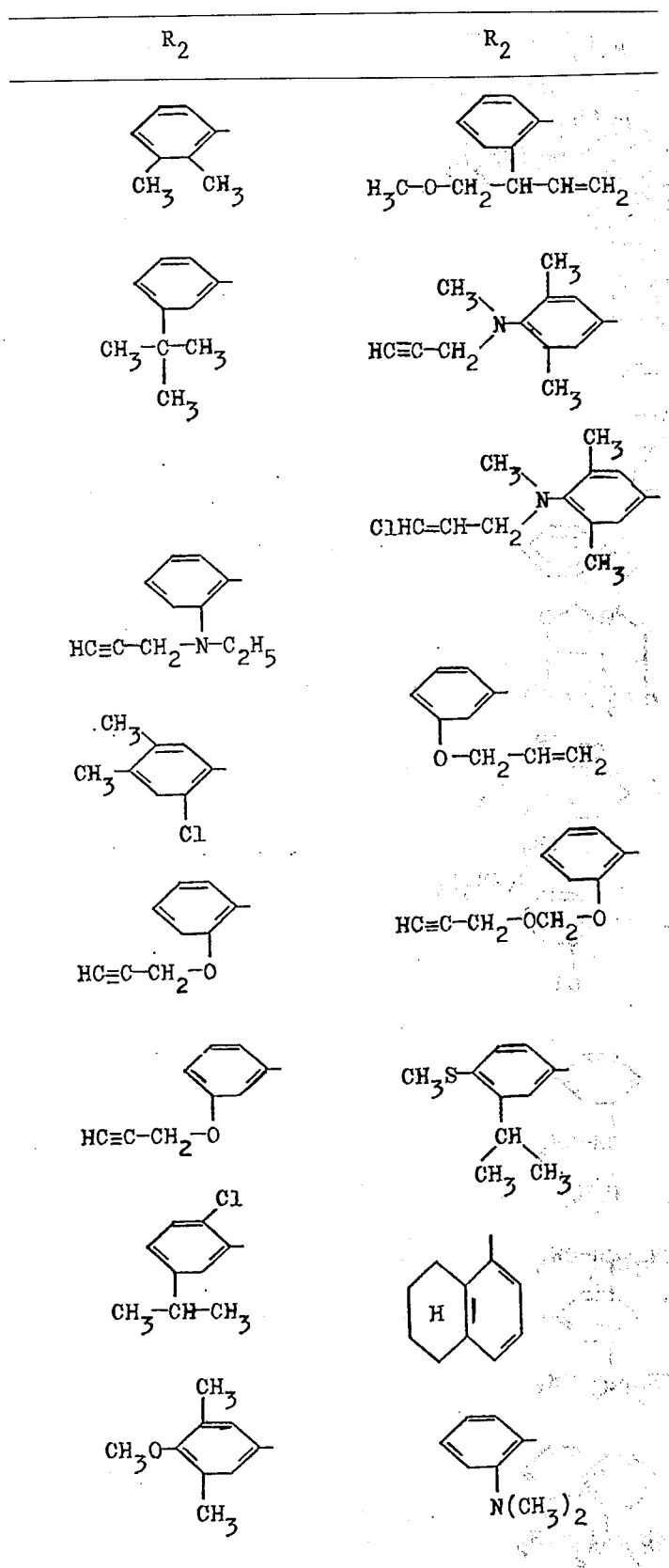

-continued
| $R_2$ | $R_2$ |
|---|---|
| 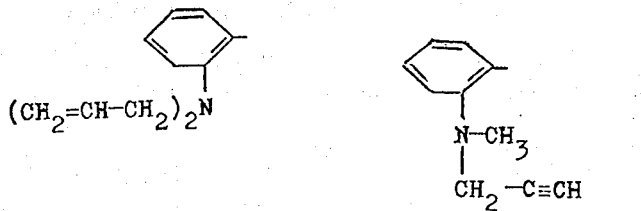 | 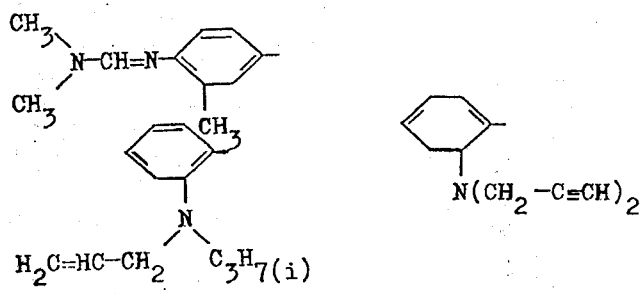 |
| 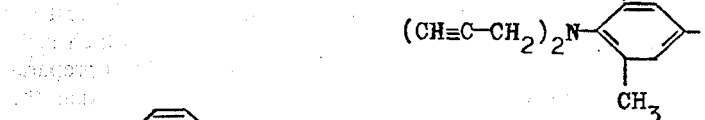 | 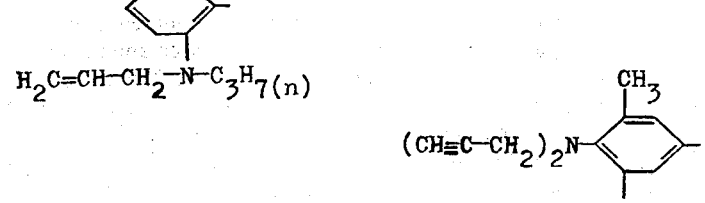 |
|  |  |
| 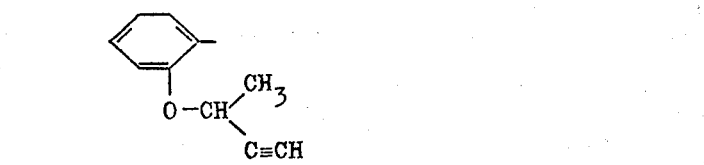 | |
| 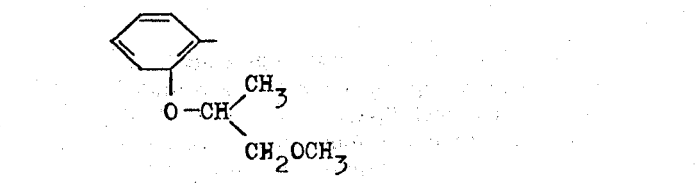 | |

EXAMPLE 2

A. Insecticidal ingest poison action

Cotton and potato plants were sprayed with a 0.05% aqueous emulsion (obtained from a 10% emulsifiable concentrate). After the coating had dried, the cotton plants were populated with Spodoptera littoralis or Heliothis virescens larvae $L_3$ and the potato plants with Colorado potato bettle larvae (*Leptinotarsa Decemilineata*). The test was carried out at 24°C and 60% relative humidity. In the above test, the compounds according to Example 1 displayed good ingest poison action against *Spodoptera littoralis*, Heliothis and *Leptinotarsa decemlineata*.

B. Systemic insecticidal action

To determine the systemic action, rooted bean plants (*Vicia fabae*) were put into a 0.01% aqueous active substance solution (obtained from a 10% emulsifiable concentrate). After 24 hours, aphids (*Aphis fabae*) were placed on the parts of the plant above the soil. The aphids were protected from contact and gas action by means of a special device. The test was carried out at 24°C and 70% relative humidity. In the above tests the compounds according to Example 1 displayed good insecticidal ingest poison and systemic insecticidal action.

EXAMPLE 3

Action against *Chilo suppresalis*

Six rice plants at a time of the variety Caloro' were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rate of application: 8 kg of active substance per hectare). Evaluation of the insecticidal action took place 10 days after application of the granules.

The compounds according to Example 1 were active in the above test against *Chilo suppressalis*.

EXAMPLE 4

Action against soil insects

Sterilised compost earth is homogeneously mixed with a wettable powder containing 25% of active substance so as to give concentrations of 16, 8, 4, 2, and 1 ppm. Young zucchetti and cabbage plants were planted in the prepared soil and immediately infested with five *Aulacophora femoralis* larvae (age: 15 d/25°C) and 15 *Chortophila brassicae* (cabbage fly) eggs. A third corresponding soil sample is provided with slices of apple as feed and populated with 5 *Pachnoda savignyi* larvae (20 d/25°C). Mortality inspection is carried out 10 days after application and infestation.

The screening test with caterpillars (Agrotis Y-$L_2$) proceeds in analogous manner, except that the concentrations are 40, 20, and 10 ppm. Mallow leaves are used as feed. In the above test, the compounds according to Example 1 were active against *Aulacophora femoralis*, *Chortophila brassicae*, *Pachnoda savigny*, and *Agrotis* larvae.

EXAMPLE 5

Action against ticks

A. *Rhipicephalus bursa*

Five adult ticks and 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be adsorbed by the cotton wool.

In the case of the adults evaluation took place after 2 weeks, and in that of the larvae after 2 days. Each test was repeated twice.

B. *Boophilus microplus* (larvae)

Tests were carried out in each case with 20 OP-sensitive larvae using an analogous dilution series as in the case of test A. (The resistance refers to the tolerability of Diazinon).

The compounds according to Example 1 acted in these tests against adults and larvae of *Rhipicephalus bursa* sensitive and OP-resistant larvae of *Boophilus microplus*.

EXAMPLE 6

Acaracidal action

*Phaseolus vulgaris* (dwarf beans) have an infested piece of leaf from a mass culture of *Tetranychus urticae* placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25°C. The compounds according to Example 1 were active in the above test against eggs, larvae and adults of *Tetranychus urticae*.

EXAMPLE 7

Action against soil nematodes

To test the action against soil nematodes, the active substance in the concentration indicated in each case is applied to and intimately mixed with soil infected with root gall nematodes (*Meloidgyne Avenaria*). Immediately afterwards, tomato cuttings are planted in the thus prepared soil in a series of tests and after a waiting time of 8 days tomato seeds are sown in another test series. In order to assess the nematocidal action, the galls present on the roots are counted 28 days after planting and sowing respectively. In this test the compounds according to Example 1 display good action against *Meloidgyne Avenaria*.

I claim:

1. A compound of the formula

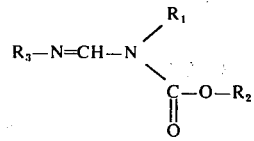

or salts thereof, wherein $R_1$ represents $C_1$–$C_4$ alkyl, $R_2$ represents $\alpha$-naphthyl or phenyl substituted by halogen, $C_1$–$C_5$ alkyl, $C_1$–$C_4$ haloalkyl, $C_1$–$C_4$ alkoxy, alkoxyalkyl with one to four carbon atoms in each alkyl moiety, $C_1$–$C_4$ alkylthio, $C_3$–$C_4$ alkynyloxy, di-($C_1$–$C_4$) alkylamino, di-($C_3$–$C_5$) alkenylamino, di-($C_3$–$C_5$) alkynylamino, hydroxy, cyano, nitro, cyclopentyl, mono-(C₁–C₄) alkylaminomethyleneamino, di-(C₁–C₄) alkylaminomethyleneimino,

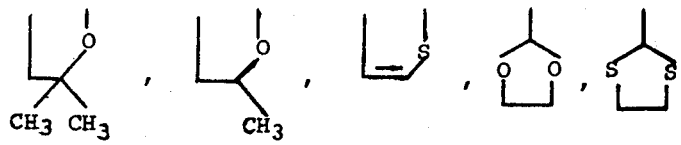

or

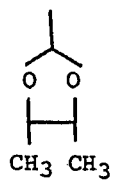

groups, and R₃ represents C₁₋C₄ alkyl.

2. The compound according to claim 1, wherein R₁ represents methyl, R₂ represents α-naphthyl, 2-methylphenyl, 3-methylphenyl, 2-chlorophenyl, 2-isopropylphenyl, 3-isopropylphenyl, 3-methyl-5-isopropylphenyl, 2-chloro-5-tert. butylphenyl, 3,4-dimethylphenyl, 3,4,5-trimethylphenyl, 3,5-dimethyl-4-methylthiophenyl, 3,5-di-tert.butylphenyl, 2-isopropoxyphenyl, 2-allyloxyphenyl, 3-methyl-4-dimethylaminophenyl, 3,5-dimethyl-4-dimethylaminophenyl, 3,5-dimethyl-4-diallylaminophenyl, 1,3-dioxolan-2-yl-phenyl, 1,3-diothiolan-2-yl-phenyl, (4,5-dimethyl-1,3-dioxolan-2-yl)-phenyl, 3-(1-methylbutyl)-phenyl, 2-sec.butylphenyl, 3-(1-ethylpropyl)-phenyl, 2,3-xylyl, 3-tert.butylphenyl, 3-sec.butylphenyl, 3,5-diisopropylphenyl, 2-chloro-5-isopropylphenyl, 3,5-dimethyl-4-methoxyphenyl, 3-allyloxyphenyl, 2-propargyloxymethoxyphenyl, 2-γ-methylthiopropylphenyl, 3-(α-methoxymethyl)-2-propenylphenyl, 4-(methyl-propargylamino)-3,5-xylyl, 4-(methyl-γ-chloroallylamino)-3,5-xylyl, 2-(ethylpropargylamino)-phenyl, 2-chloro-4,5-dimethylphenyl, 2-(2-propionyloxy)-phenyl, 3-(2-propinyloxy)-phenyl, 2-dimethylaminophenyl, 2-diallylaminophenyl, 3-methyl-4-dimethylaminomethyleneiminophenyl, 3-dimethylaminomethyleneiminophenyl, 3-isopropyl-4-methyl-thiophenyl, 5,6,7,8-tetrahydronaphthyl, 2-(methyl-propargylamino)-phenyl, 2-(dipropargylamino)-phenyl, 4-(dipropargylamino)-3-tolyl, 4-(dipropargylamino)-3,5-xylyl, 2-(allylisopropylamino)-phenyl, 3-(allyl-isopropylamino)-phenyl, 3-methoxymethoxyphenyl, 2-cyclopentylphenyl, 2-(1-butin-3-yloxy)-phenyl or 2-(1-methoxy-2-propoxy)-phenyl,

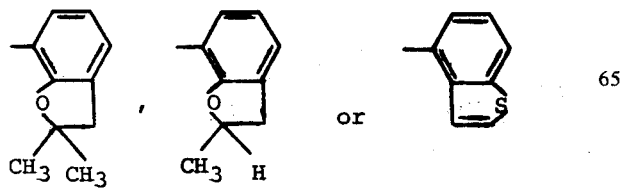

3. A compound according to claim 2, of the formula

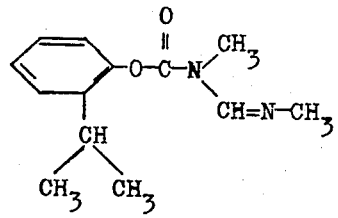

4. A compound according to claim 2, of the formula

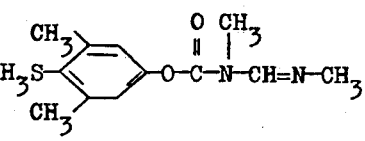

5. A compound according to claim 2, of the formula

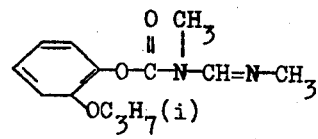

6. A compound according to claim 2, of the formula

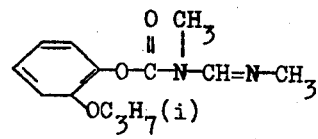

* * * * *